(12) United States Patent
McGuin

(10) Patent No.: US 8,887,313 B2
(45) Date of Patent: Nov. 18, 2014

(54) WRAP FOR HUMAN APPENDAGE

(71) Applicant: Aaron McGuin, Osceola, IN (US)

(72) Inventor: Aaron McGuin, Osceola, IN (US)

(*) Notice: Subject to any disclaimer, the term of this patent is extended or adjusted under 35 U.S.C. 154(b) by 0 days.

(21) Appl. No.: 14/090,531

(22) Filed: Nov. 26, 2013

(65) Prior Publication Data

US 2014/0075658 A1 Mar. 20, 2014

Related U.S. Application Data

(63) Continuation-in-part of application No. 13/409,821, filed on Mar. 30, 2012, now abandoned.

(51) Int. Cl.
*A41D 13/00* (2006.01)
*A41D 13/06* (2006.01)
*A41D 13/08* (2006.01)

(52) U.S. Cl.
CPC ............. *A41D 13/06* (2013.01); *A41D 13/081* (2013.01); *A41D 13/08* (2013.01)
USPC .............................................................. 2/16

(58) Field of Classification Search
USPC ................... 2/16, 22, 24, 455, 170, 242, 911; 40/633, 665; 283/75, 81; 602/20, 21, 602/23; 128/878, 879
See application file for complete search history.

(56) References Cited

U.S. PATENT DOCUMENTS

| | | | | |
|---|---|---|---|---|
| 2,954,620 A * | 10/1960 | Schneider | ........................ | 40/633 |
| 3,153,869 A * | 10/1964 | Twentier | ......................... | 40/633 |
| 6,338,723 B1 * | 1/2002 | Carpenter et al. | .............. | 602/75 |
| 6,349,493 B1 * | 2/2002 | Newman et al. | ................ | 40/633 |
| 8,099,889 B2 * | 1/2012 | Landsman et al. | ............. | 40/633 |
| 8,490,307 B2 * | 7/2013 | Landsman et al. | ............. | 40/633 |

* cited by examiner

*Primary Examiner* — Tejash Patel
(74) *Attorney, Agent, or Firm* — R. Tracy Crump

(57) ABSTRACT

An appendage wrap having a sequential set of graphic instruction steps printed across the length of the wrap on one or both sides for explaining and illustrating how a user is to apply the wrap to a specific appendage. Each individual instruction step is readily visible to the user and is easily discernable as the wrap is unrolled and wound around the appendage. Text instructions provide concise directions to the user. Simply illustrations of the appendage (hand graphics) provide a visual reference to the user for the direction and location where the wrap will be wound. Arrows are used to visually guide the user as wrap is unrolled and wound around the wrist.

3 Claims, 19 Drawing Sheets

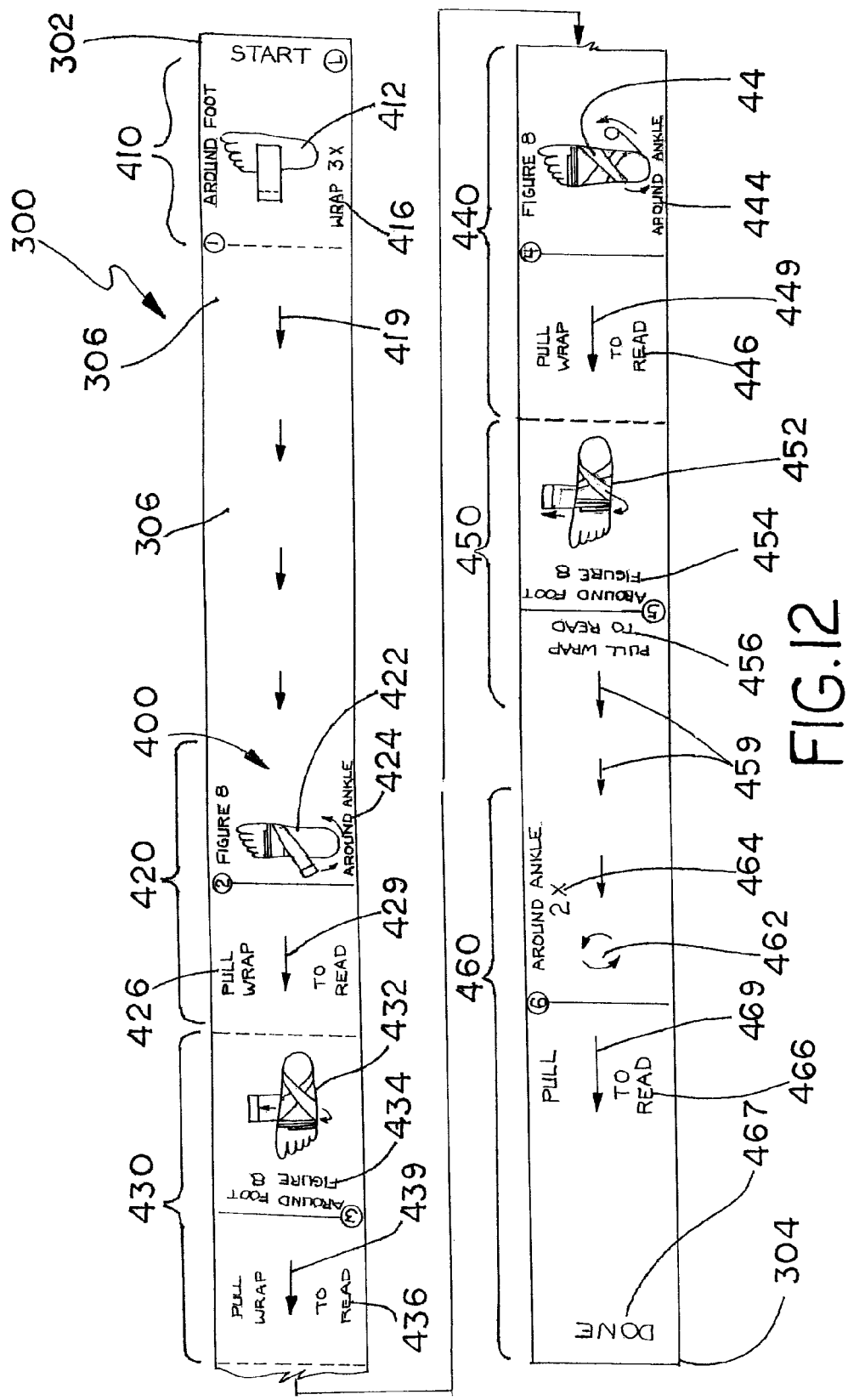

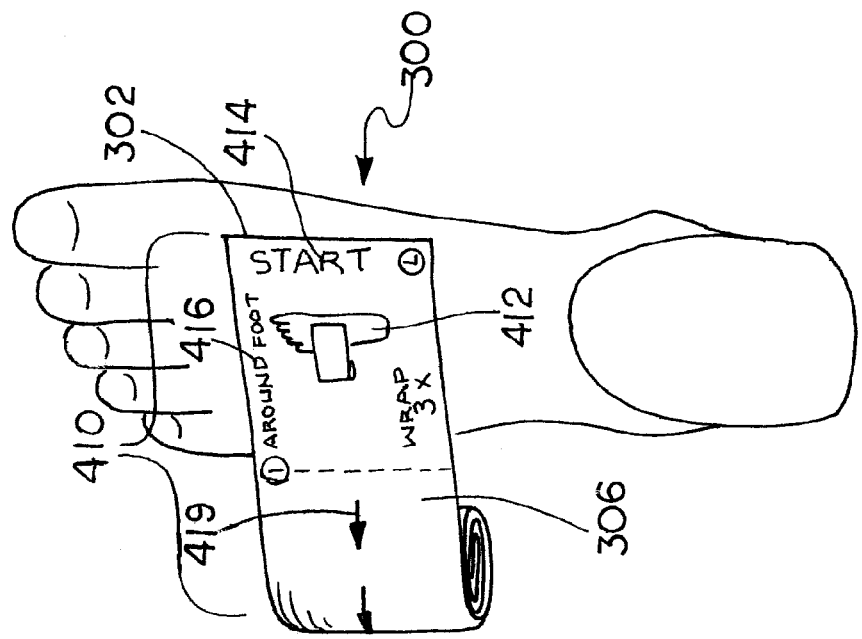
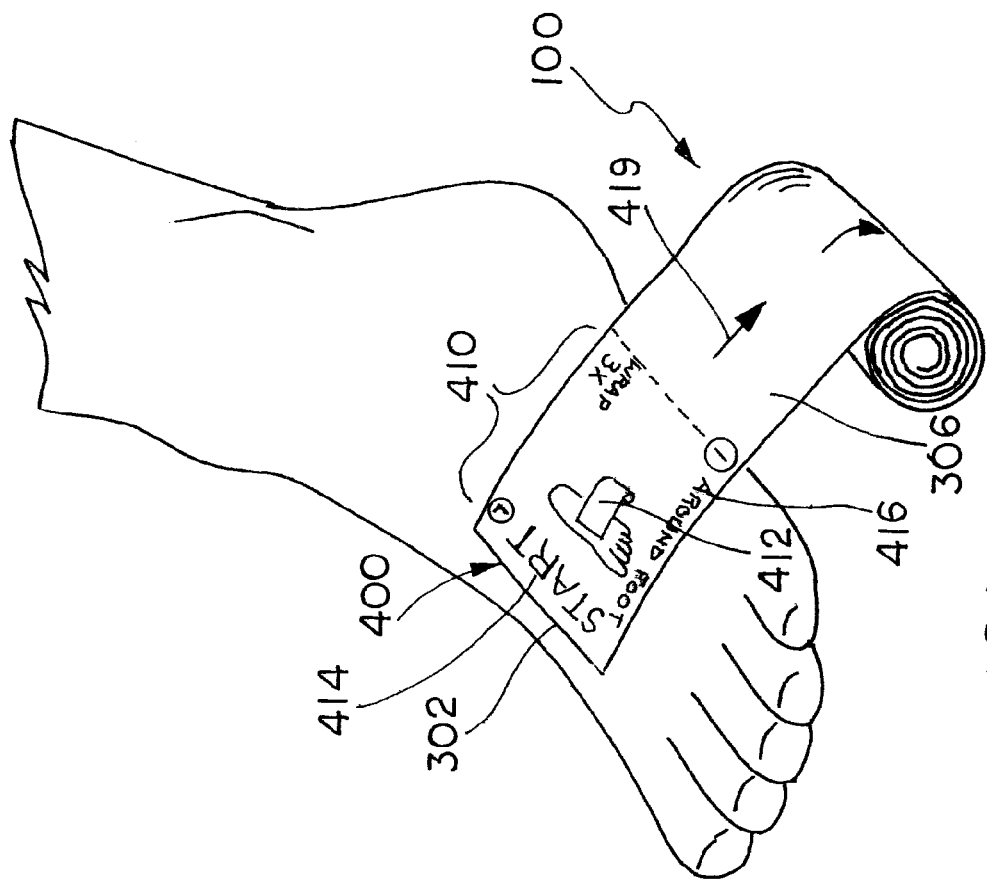
FIG.14
FIG.13

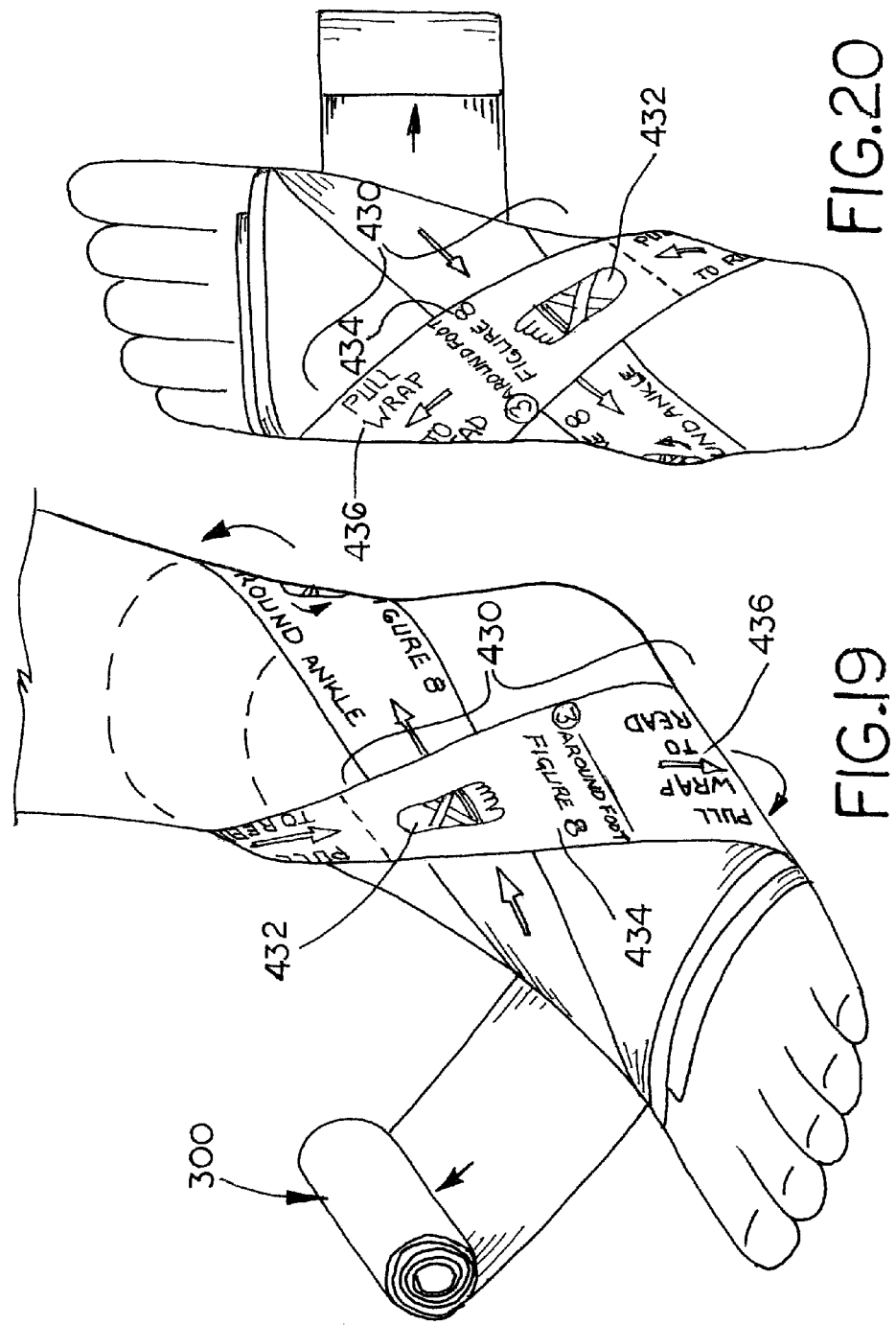

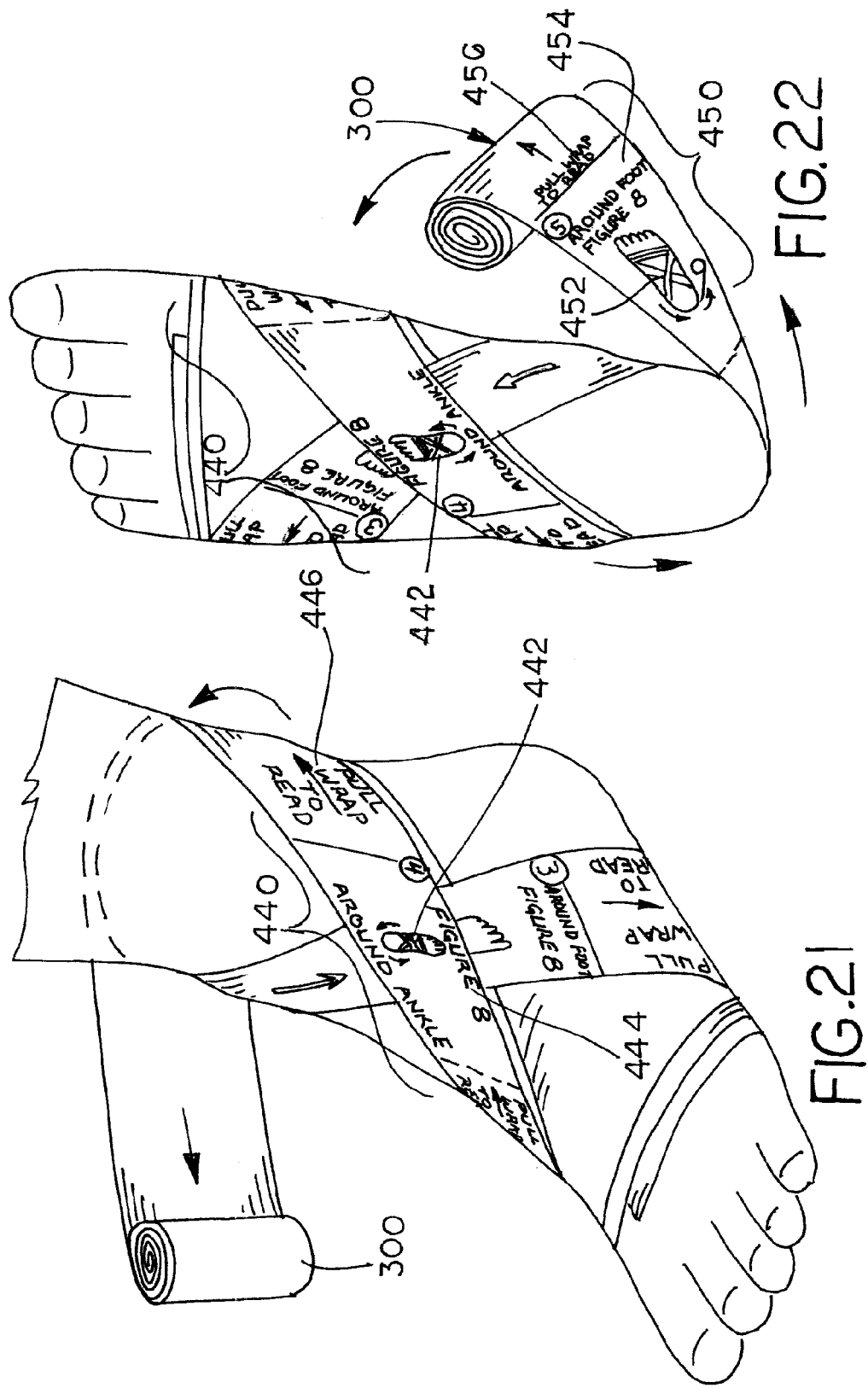

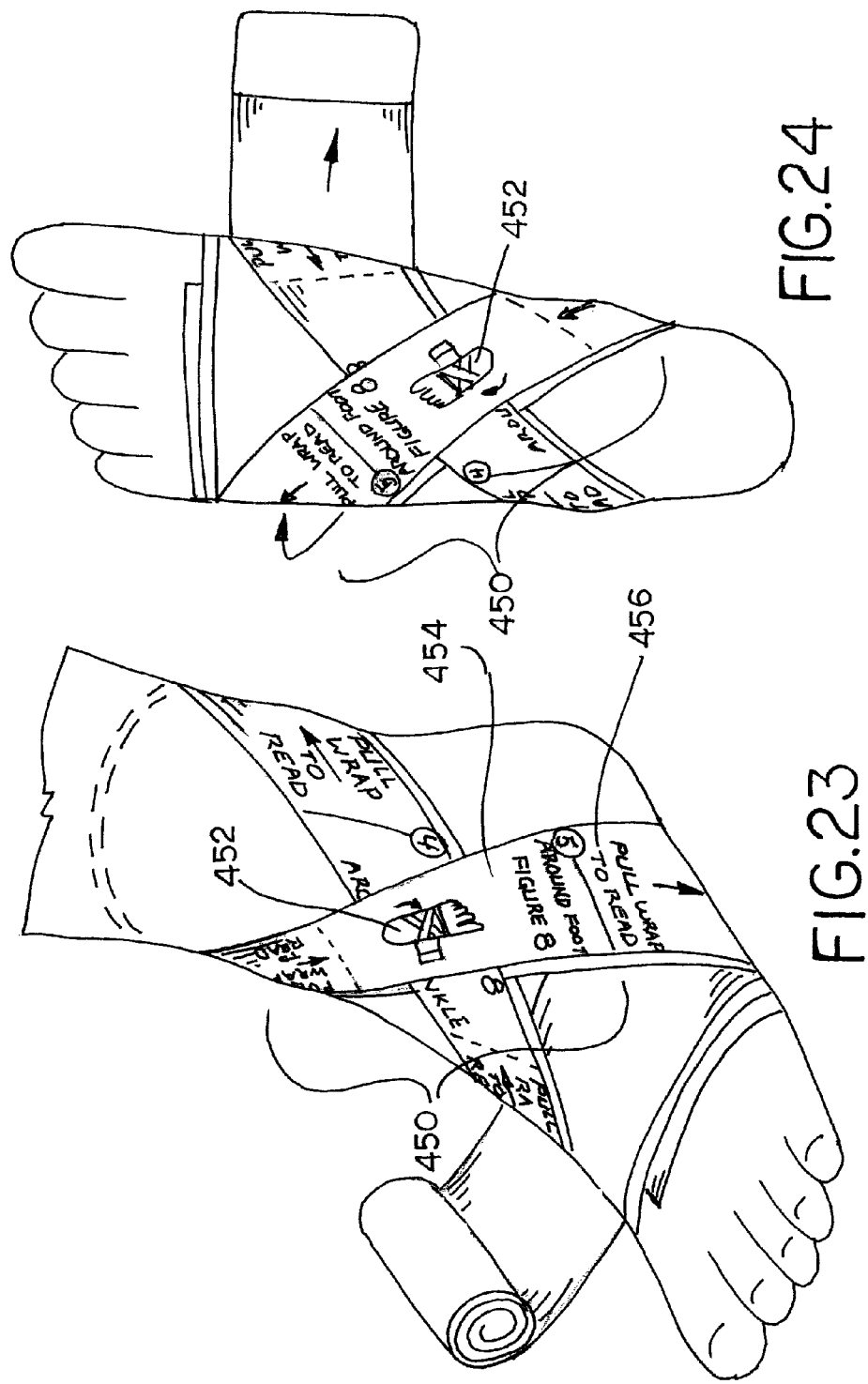

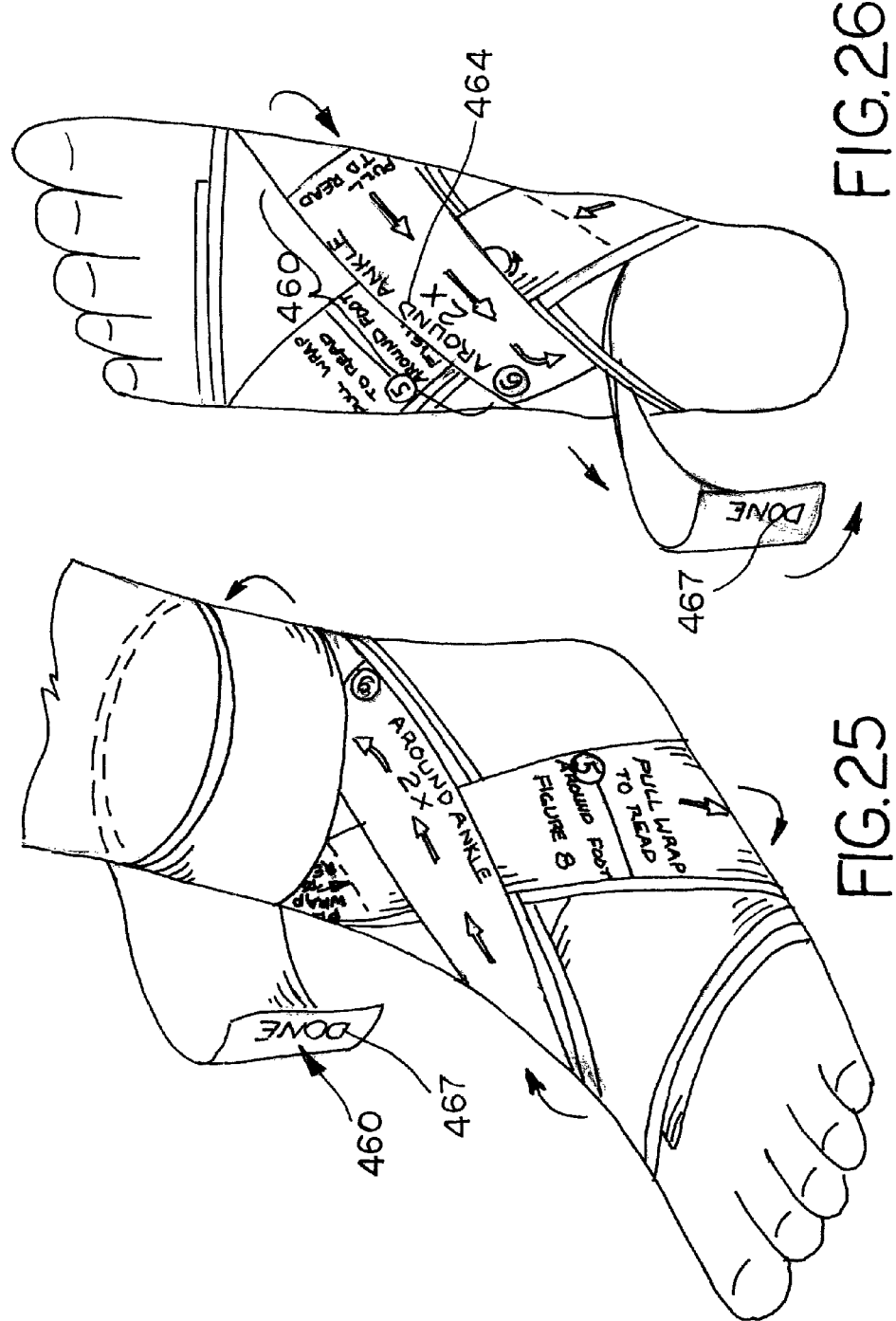

WRAP FOR HUMAN APPENDAGE

This is a continuation-in-part of pending U.S. patent application, Ser. No. 13/409,821 filed on Mar. 30, 2012.

This invention relates fabric wraps for use human appendages, namely hands and feet, and in particular illustrated wraps depicting instructions for donning the wrap around a particular appendage.

BACKGROUND AND SUMMARY OF THE INVENTION

Cloth and elastic wraps are commonly used to bind and support human appendages, hands and feet for various purposes. Cloth athletic hand wraps are commonly used by boxers and martial artist to support and protect their hands. Elastics wraps are used on both hands and feet for similar purposes. Heretofore, the use and application of a cloth or elastic wrap to an appendage required specific knowledge of how to properly apply the wrap about the appendage. The technique for wrapping a hand or foot can be difficult for the inexperienced, particularly when the wrap is self applied.

The present invention seeks to provide an appendage wrap having a sequential set of graphic instruction steps printed across the length of the wrap on one or both sides for explaining and illustrating how a user is to apply the wrap to a specific appendage. The wraps of this invention allow novice user's to quickly and properly apply a wrap to a particular appendage. One embodiment of this invention is specifically intended as a hand wrap for boxers and martial artists. Another embodiment is specifically intended as a foot and ankle wrap.

Each of the instruction sets printed on the wraps include a set of sequential instruction steps that was spaced along the length of the wrap to guide the application of the wrap to an appendage, whether the user's own appendage or a third person's appendage. Each individual instruction step is readily visible to the user and is easily discernable as the wrap is unrolled and wound around the appendage. Text instructions provide concise directions to the user. Simply illustrations of the appendage (hand graphics) provide a visual reference to the user for the manner, direction and location where the wrap will be wound. Arrows are used to visually guide the user as wrap is unrolled and wound around the appendage.

The above described features and advantages, as well as others, will become more readily apparent to those of ordinary skill in the art by reference to the following detailed description and accompanying drawings.

BRIEF DESCRIPTION OF THE DRAWINGS

The present invention may take form in various system and method components and arrangement of system and method components. The drawings are only for purposes of illustrating exemplary embodiments and are not to be construed as limiting the invention. The drawings illustrate the present invention, in which:

FIG. 12 is a top view of a second embodiment of this invention, showing the foot/ankle wrap unrolled;

FIG. 13 is a perspective view of the wrap of FIG. 12 being applied to a human foot, showing the first instruction step;

FIG. 14 is a top view of the wrap of FIG. 12 being applied to a human foot, showing the first instruction step;

FIG. 19 is a perspective view of the wrap of FIG. 12 being applied to a human foot, showing the third instruction step;

FIG. 20 is a top view of the wrap of FIG. 12 being applied to a human foot, showing the third instruction step;

FIG. 21 is a perspective view of the wrap of FIG. 12 being applied to a human foot, showing the fourth instruction step;

FIG. 22 is a top view of the wrap of FIG. 12 being applied to a human foot, showing the fourth instruction step;

FIG. 23 is a perspective view of the wrap of FIG. 12 being applied to a human foot, showing the fifth instruction step; and FIG. 24 is a top view of the wrap of FIG. 12 being applied to a human foot, showing the fifth instruction step;

FIG. 25 is a perspective view of the wrap of FIG. 12 being applied to a human foot, showing the sixth and final instruction step; and FIG. 26 is a top view of the wrap of FIG. 12 being applied to a human foot, showing the sixth and final instruction step.

DESCRIPTION OF THE PREFERRED EMBODIMENT

Figure 1:
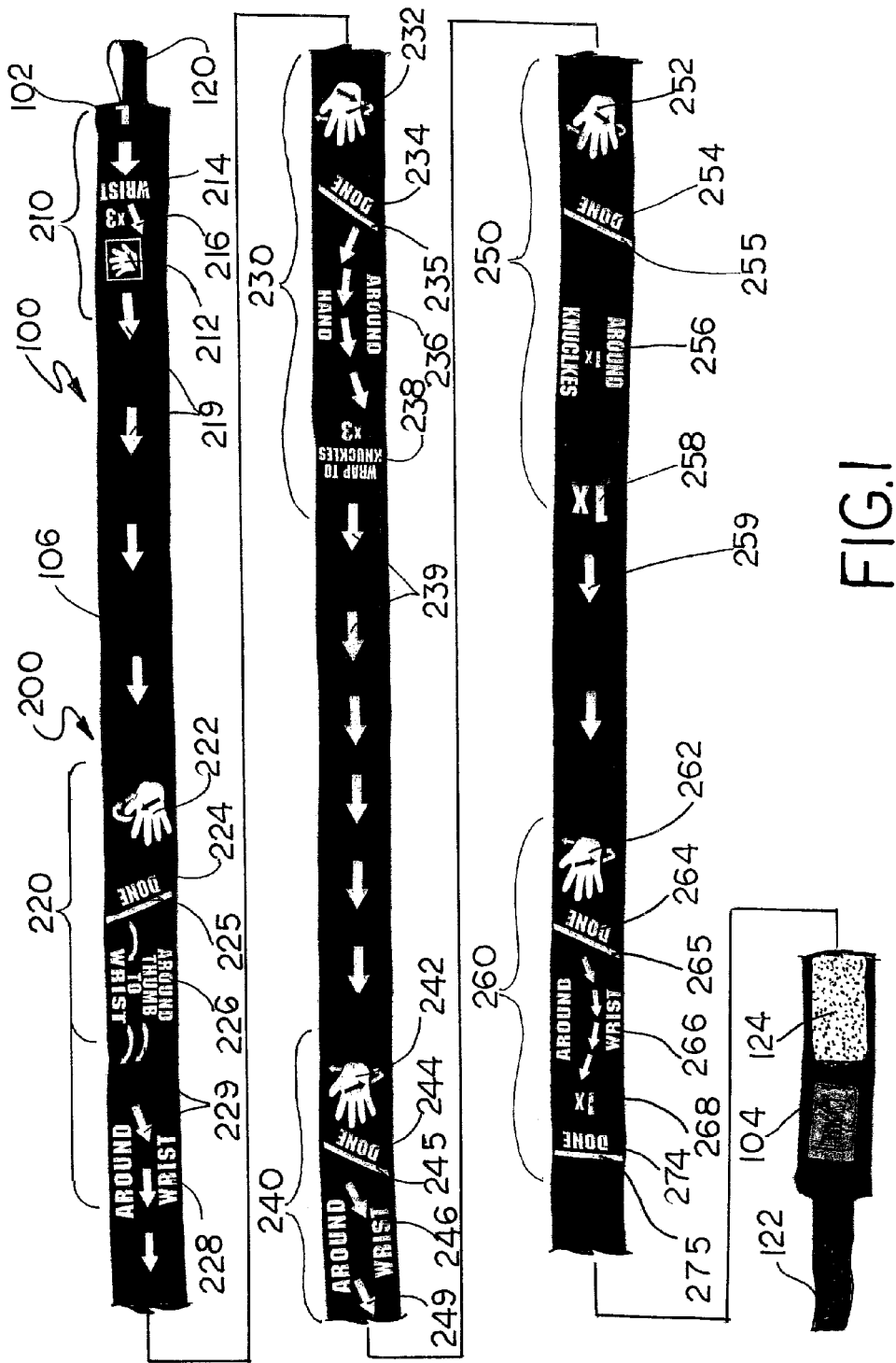
FIG. 1 is a top view of one embodiment of this invention, showing the hand wrap unrolled.

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical, structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

The drawings illustrate two different embodiments of this invention. Each wrap embodying this invention generally consists of an elongate strip of fabric having written and graphic instructions (collectively, an "instruction sets") printed on one or both sides for explaining and illustrating how the wrap is to be applied to a specific appendage. The printed instruction sets are grouped into sequential instruction blocks that are spaced across the entire length of the wrap. Each instruction block using pictures, letters, numbers, symbols, word text to depict each stage or step of the wrap's application, which allow the user to apply the wrap to a particular appendage, whether the user's own appendage or a third person's appendage. Each sequential instruction block is readily visible to the user and is easily discernable as the wrap is unrolled and wound around the appendage. The word text of each instruction block provides concise direction to the user. The simple illustrations and arrow of each instruction block provide a visual reference to the user the direction and location where the wrap will be wound and visually guide the user as the wrap is unrolled and wound around the appendage.

The wraps themselves may be woven from any variety of natural and synthetic fibers and materials. The fabrics and materials selected for the wraps are selected for various needs specific for the wraps intended purpose. In certain embodiments, such as for ankle wraps, the wraps may require a measure of elasticity to provide compression around the appendage. The wraps are typically prepackage or staged in rolls so that the wrap can be easily wound around the appendage. After use, the wraps can be rewound back into a roll for subsequent applications.

For consistency of explanation and understanding, certain terms and conventions are used herein to describe the various embodiments of the wraps of this invention. The opposed ends of each wraps are generally identified herein as the "lead" and the "tail" end. The lead end being the first end to unwind from the rolled wrap and applied to the appendage and the tail end the last to unwind and be applied to the appendage. Each wrap also has opposed "inner" and "outer" sides. The inner sides of the wraps face the appendage around which the wrap is applied. The "outer" side is the side on which the instruction and graphics are printed. It should be noted that incertain embodiments, the instructions and graphics may be printed on both sides of the wrap to accommodate different directions of application, clockwise or counter-clockwise, or application to left or right appendages. While instruction sets may be printed on both sides of a wrap, those instruction sets are typically specific to a particular application of the wrap and both sides will in fact be designated as either the "inner" side or the "outer" side for any particular application of the wrap.

Referring now to the drawings, FIGS. 1-11 show a first embodiment of the wrap of this invention, designated generally as reference numeral 100. As shown, wrap 100 is a hand wrap 100 of the type used by boxers and martial artists. Wrap 100 is fashioned as a conventional "boxer's hand wrap" and consists of a strip of woven cloth with serialized graphic instruction sets 110 printed on both sides. The cloth fabric is typically a cotton/linen, but may be constructed of any suitable woven fabric or material. A thumb loop 120 extends from the lead end 102 of wrap 100. The tail end 104 of wrap 100 uses hook and loop fasteners to secure the tail end of the wrap around the user's hand. A tab of hook material 122 extends longitudinally from the tail end 104 of wrap 100. An elongated section of loop material 124 is sewn to the tail end of wrap 199.

As shown, instruction set 200 is screen printed or otherwise rendered on outer side 106 of wrap 100. Instruction set 200 explains and depicts how wrap 100 is to be applied to a user's left hand. For purposes of simplicity and brevity, the drawings only illustrate the instruction sets 200 printed on one side of wrap 100. It should be understood that another graphic instruction set is printed on the opposite side of wrap 100, which explains and depicts the application of the wrap to a user's right hand. Instruction set 200 is segmented into sequence of instruction blocks (210, 220, 230, 240, 250, 260) spaced across the length of wrap 100, which direct the user for each step of applying wrap 100. Instruction block 210 is printed adjacent the lead end 102 of wrap 100 and instruction block 260 near tail end 104. Instruction block 220, 230, 240 and 250 are selectively spaced between the lead end 102 and tail end 104, so that each instruction block is readily visible to the user and is easily discernable as wrap 100 is unrolled and wound around the hand.

Figure 2:
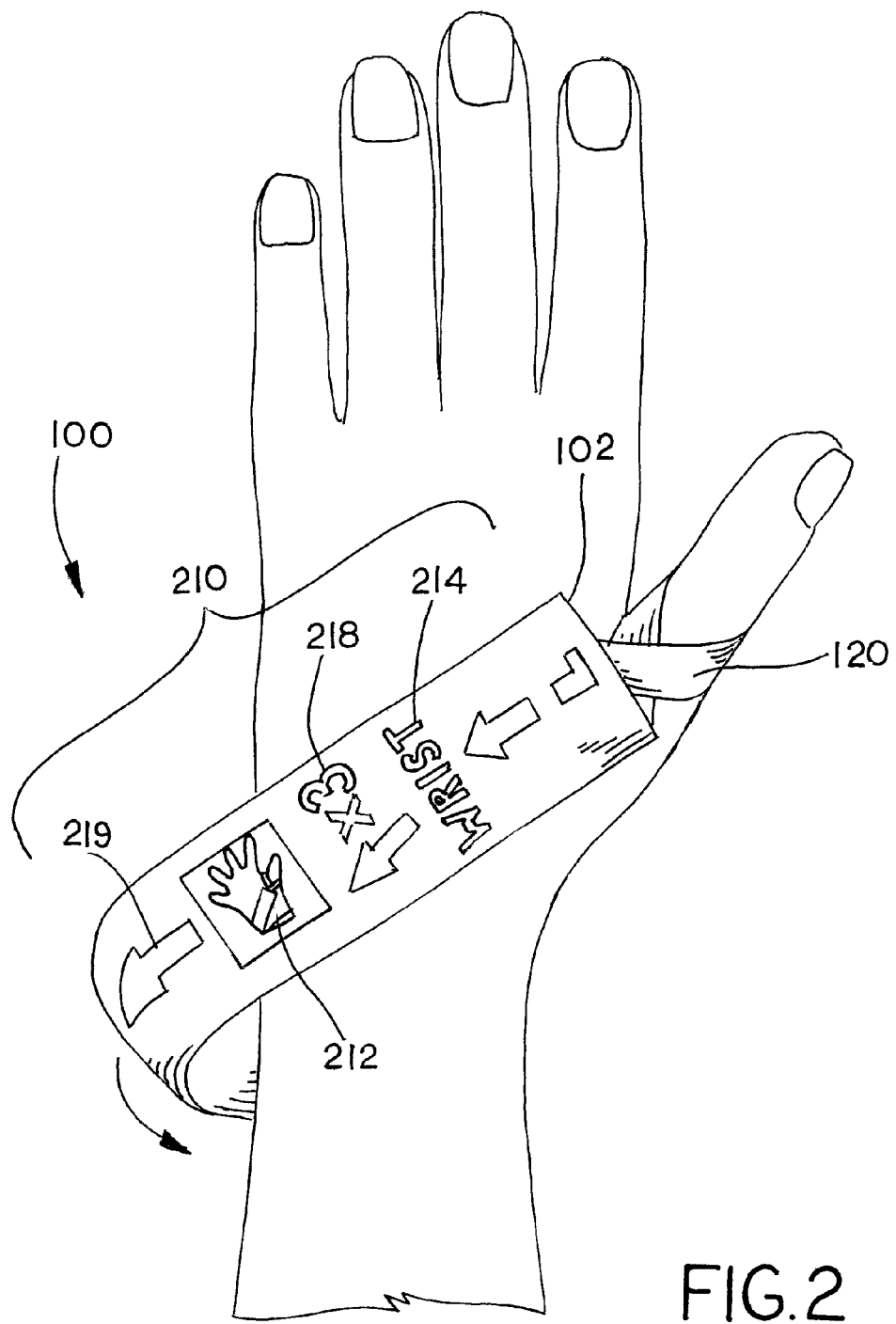
FIGS. 2 and 3 are top views of the hand wrap of FIG. 1 applied to a human hand, showing the first instruction step.
Figure 3:
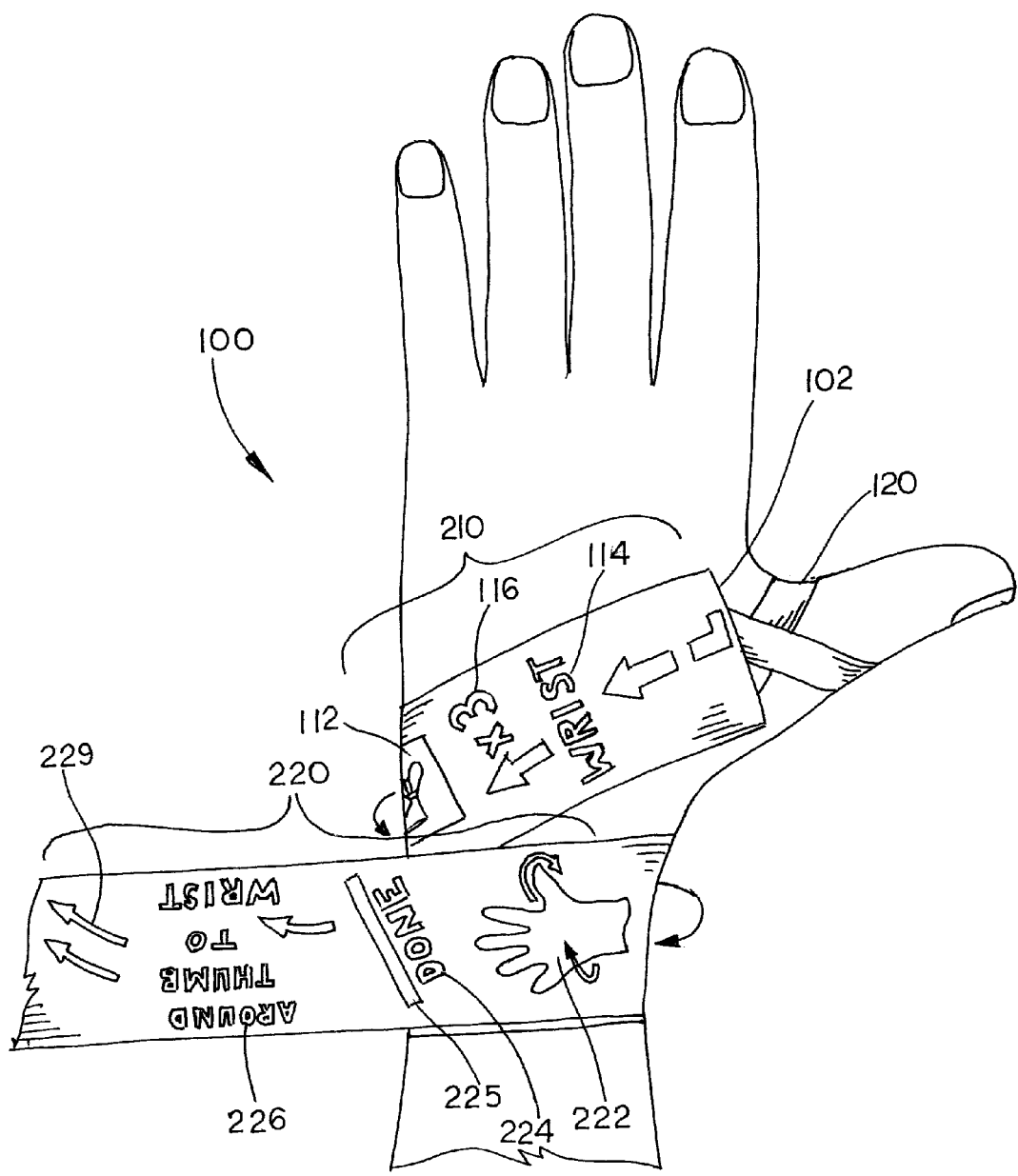

FIGS. 2-11 illustrate the steps for how wrap 100 is applied to a user's left hand and how instruction sets 200 provide a visible guide for the application of the wrap. FIGS. 2 and 3 shows the initial start for applying wrap 100 to the user's left hand. First, loop 106 is hooked over the user's thumb and wrap 100 is pulled over and across the back of user's hand. With wrap 100 overlying the back of the user's hand instruction block 210 is visible, which includes a hand graphic 212, the words "wrist" 214 and "3×" 216 and arrows 219. The words, "wrist" 214 and "3×" 216 indicate that wrap 100 will be wound around the wrist three times.

Figure 4:
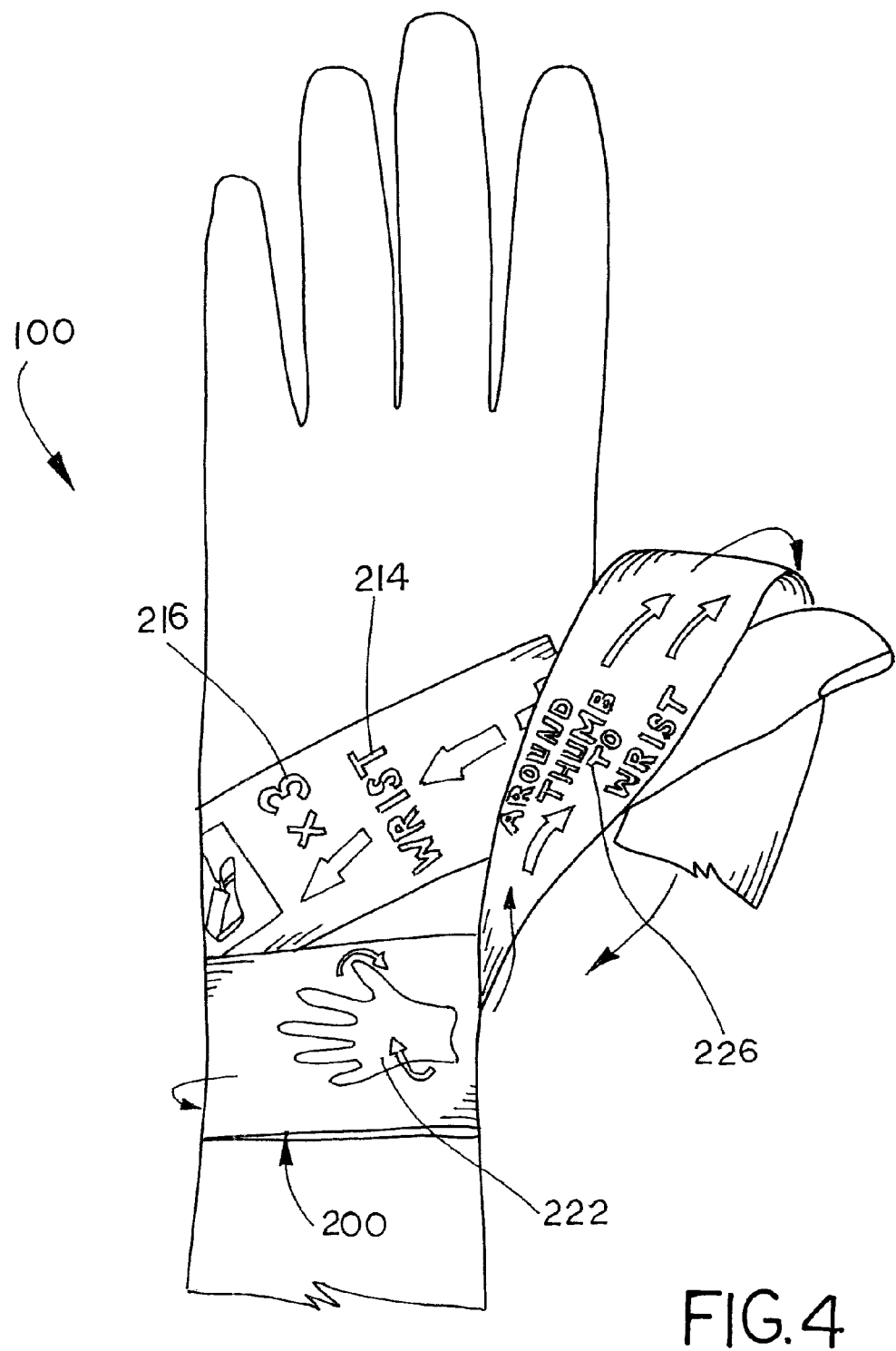
FIGS. 4 and 5 are top views of the hand wrap of FIG. 1 applied to a human hand, showing the second instruction step.
Figure 5:
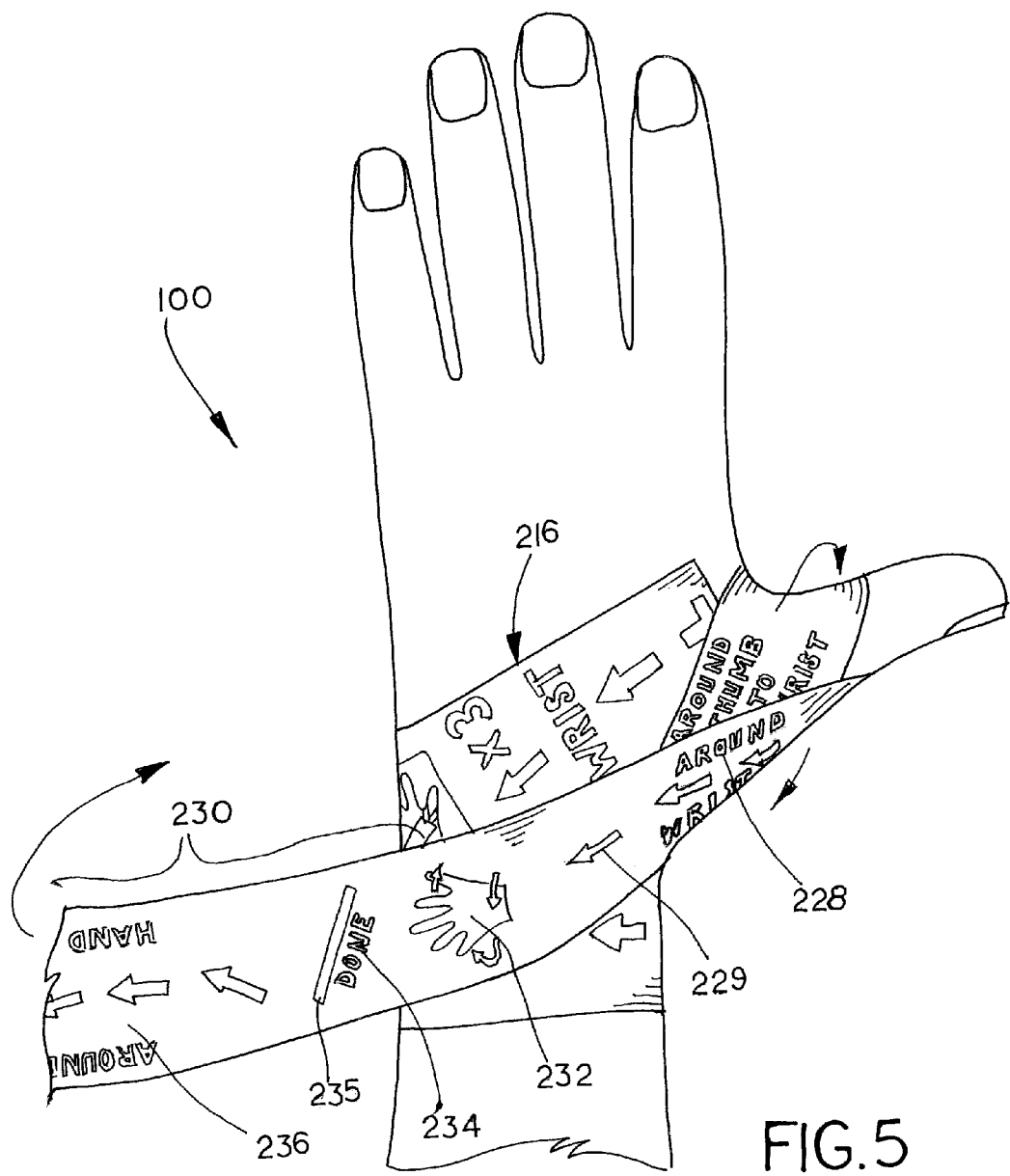

FIGS. 4 and 5 show the second step in applying the wrap to the user's hand. Once the initial step is complete, instruction block 220 is visible. Instruction block 220 includes a hand graphic 222, the word, "done" 224, a traverse stop line 225, instruction text "around thumb to wrist" 226, "around wrist" 228 and arrows 229. The instruction text "around thumb to wrist" 226 and "around wrist" 228 indicates that wrap 100 will be wound around the thumb and back across the wrist.

Figure 6:
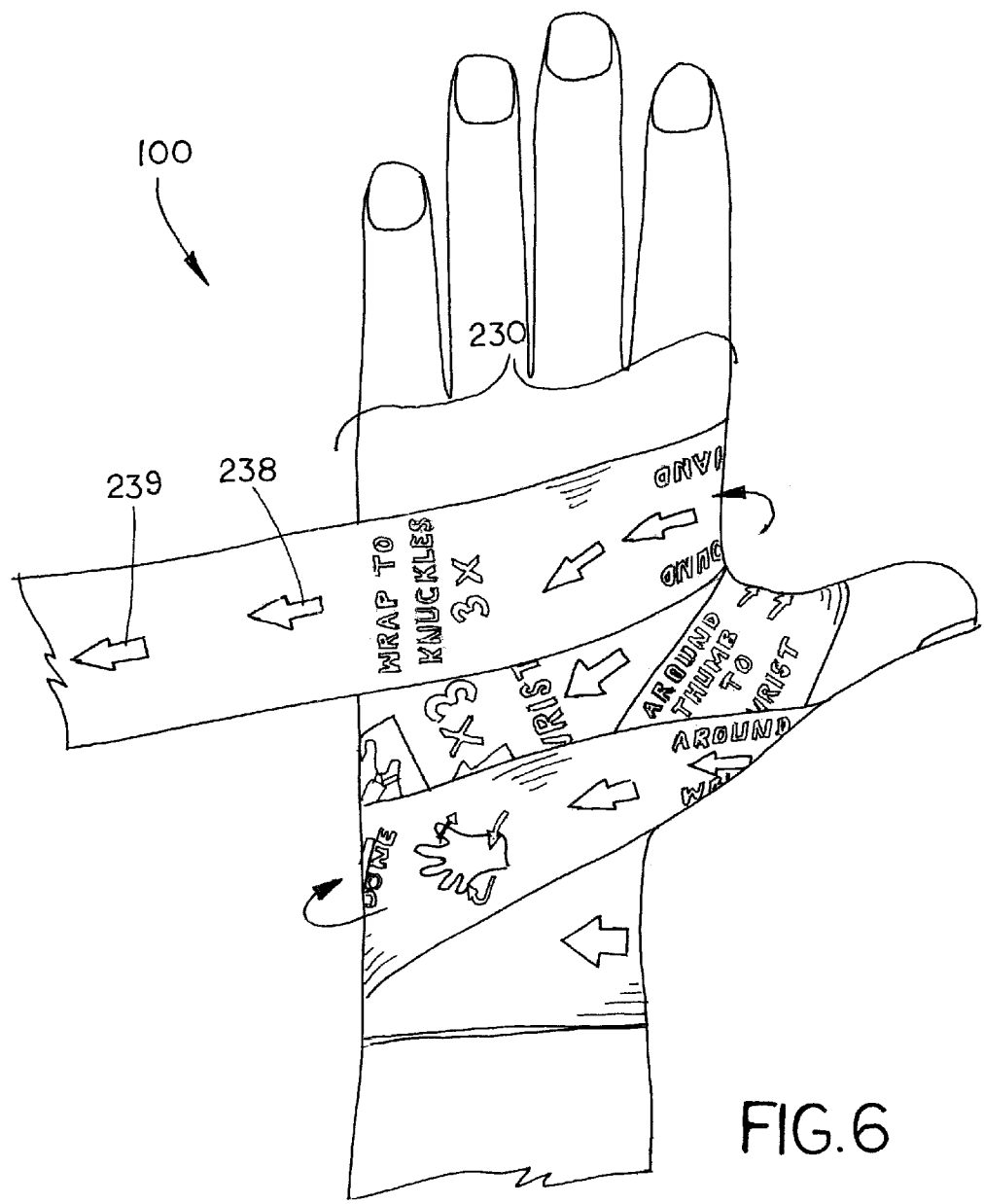
FIGS. 6 and 7 are top views of the hand wrap of FIG. 1 applied to a human hand, showing the third instruction step.
Figure 7:
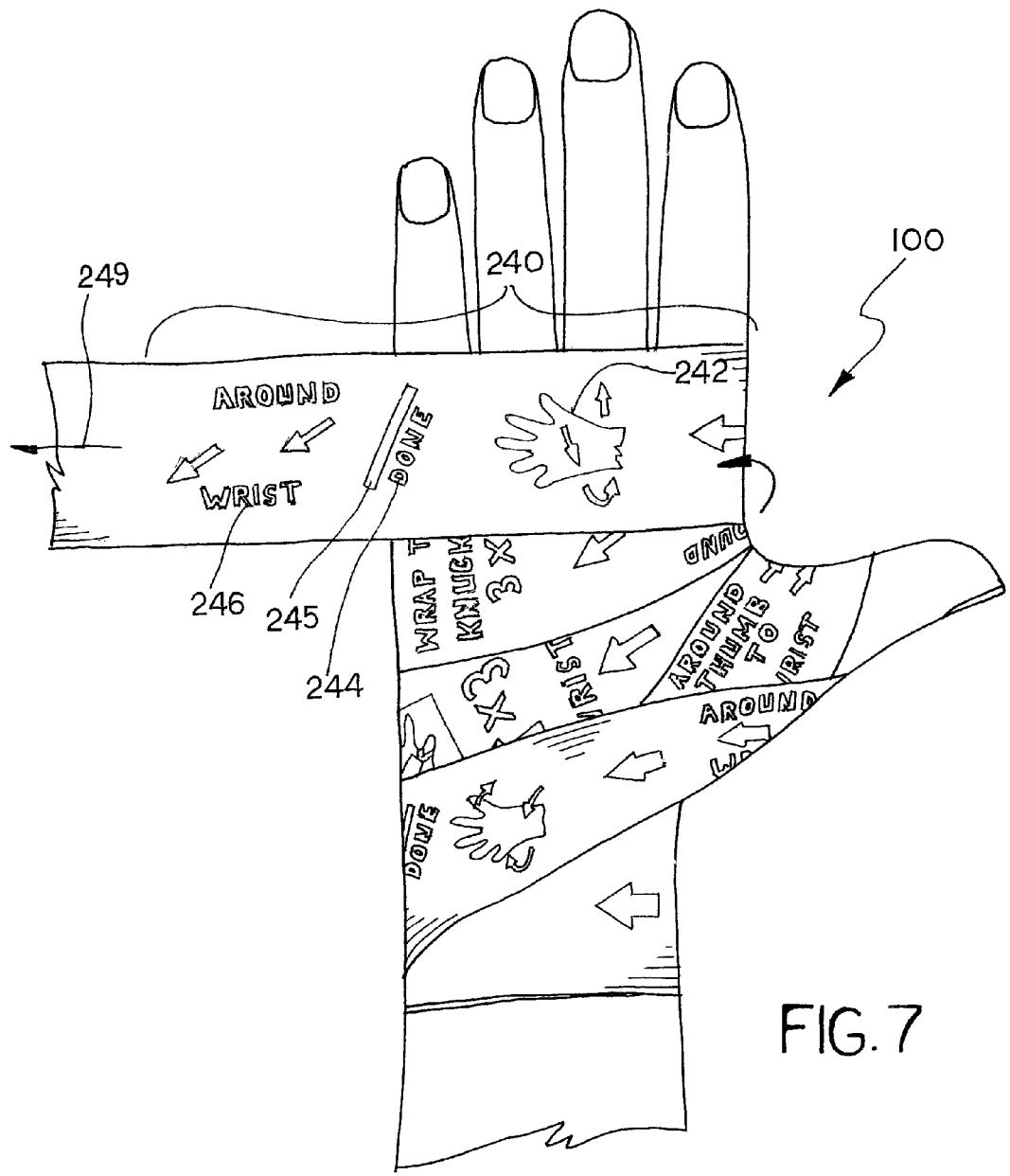

FIGS. 6 and 7 show the third step in applying the wrap to the user's hand. Once the second step is complete, instruction block 230 is visible. Instruction block 230 includes a hand graphic 232, the word, "done" 234, a stop line 235, instruction text "around hand" 236 and "wrap to knuckles ×3" 238 and arrows 239. The instruction text "around hand" 236 and "wrap to knuckles ×3" 238 indicate that wrap 100 is wound around the hand three times to cover the knuckles.

Figure 8:
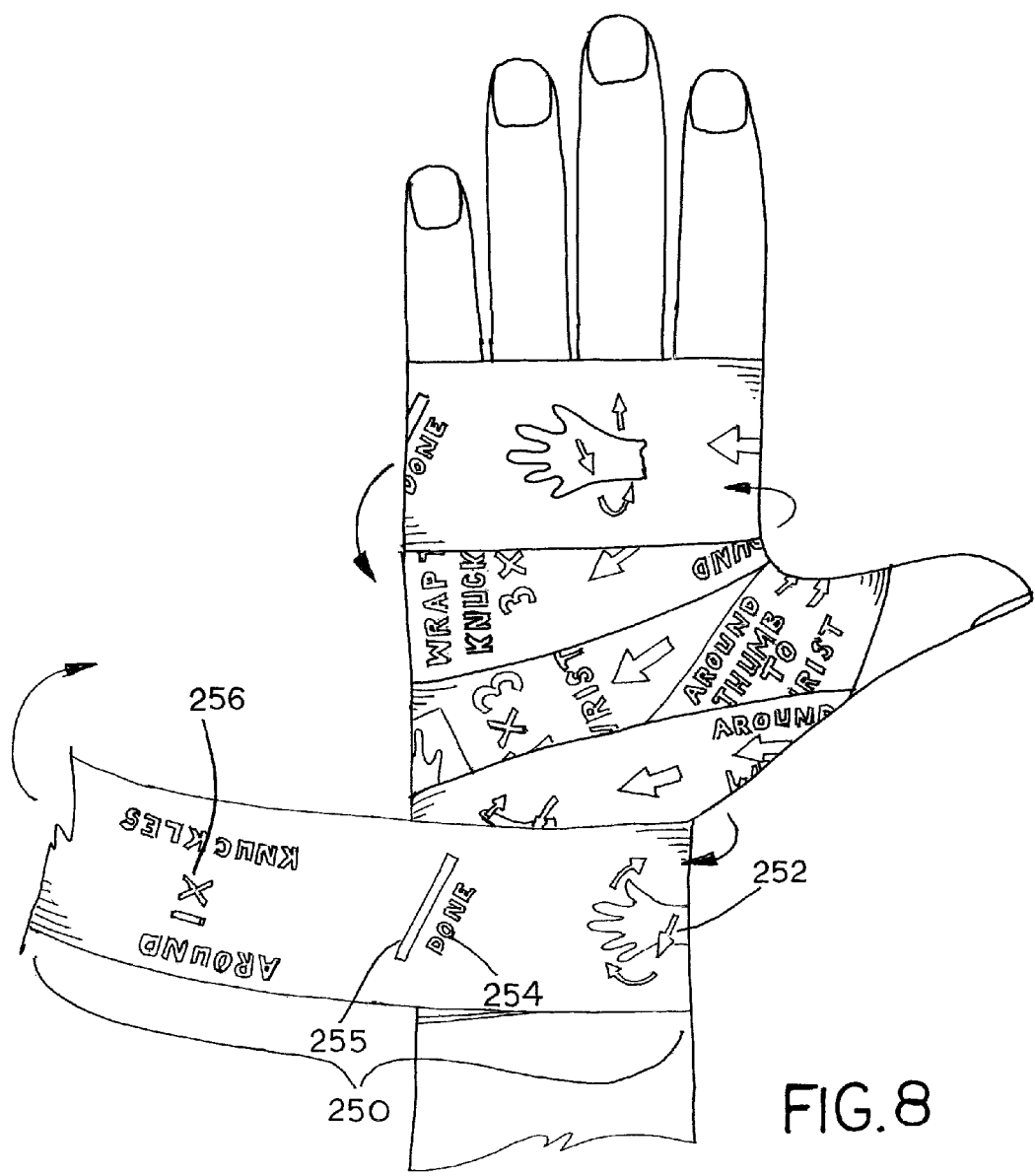
FIG. 8 is a top view of the hand wrap of FIG. 1 applied to a human hand, showing the fourth instruction step.

FIG. 8 shows a fourth step in applying the wrap to the user's hand. Once the third step is complete, instruction block 240 is visible. Instruction block 240 includes a hand graphic 242, the word, "done" 244, a stop line 245, instruction text "around wrist" 246 and arrows 239. The instruction text "around wrist" 246 indicate that wrap 100 is again wound around the wrist.

Figure 9:
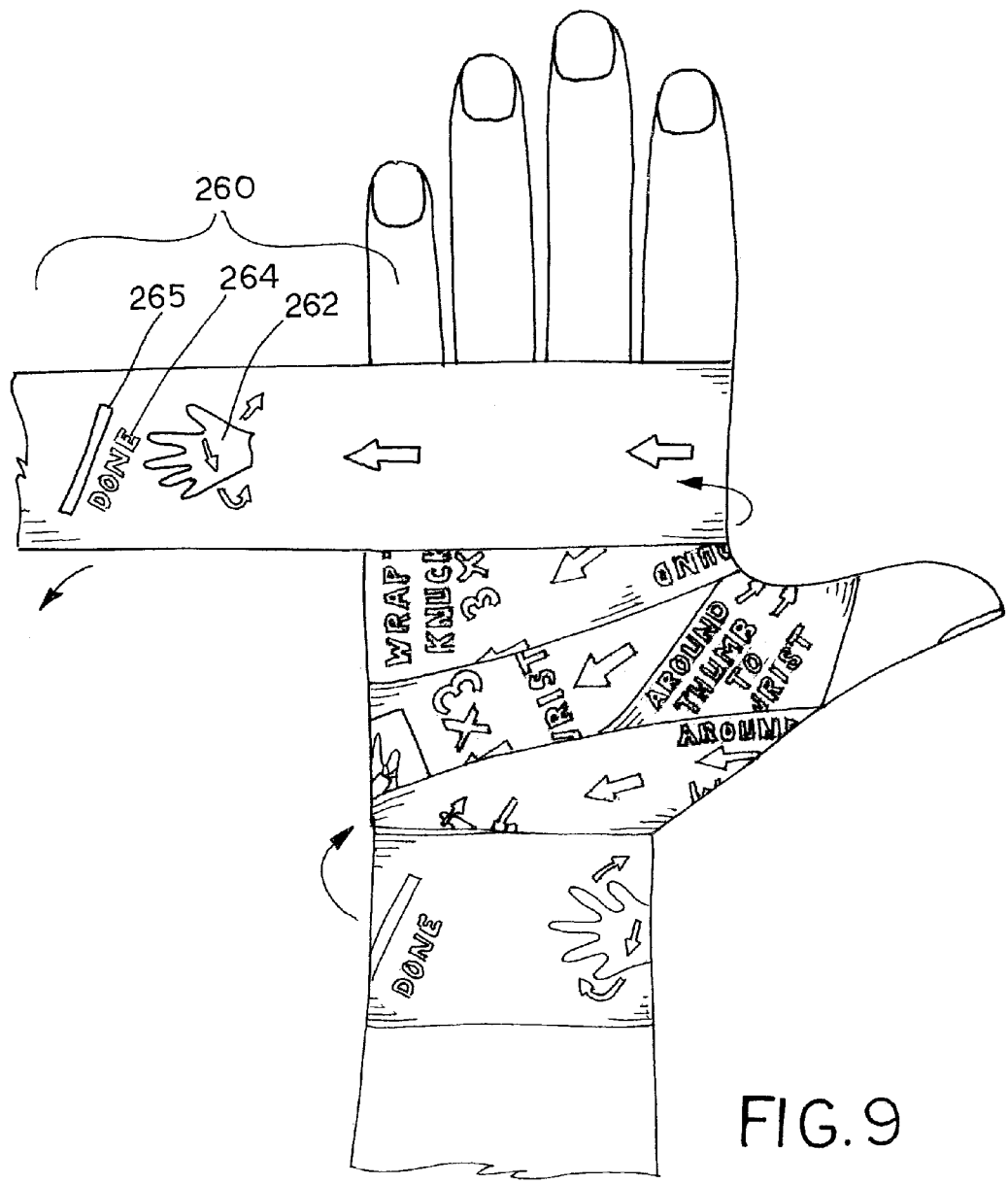
FIG. 9 is a top view of the hand wrap of FIG. 1 applied to a human hand, showing the fifth instruction step.

FIG. 9 shows the fifth step in applying the wrap to the user's hand. Once the fourth step is complete, instruction block 250 is visible. Instruction block 140 includes a hand graphic 252, the word, "done" 254, a stop line 255, instruction text "around knuckles" 256, instruction text "1×" 258 and arrows 259. The instruction text "around knuckles" 256 and "1×" 258 indicate that wrap 100 is wound around the knucles one time.

Figure 10:
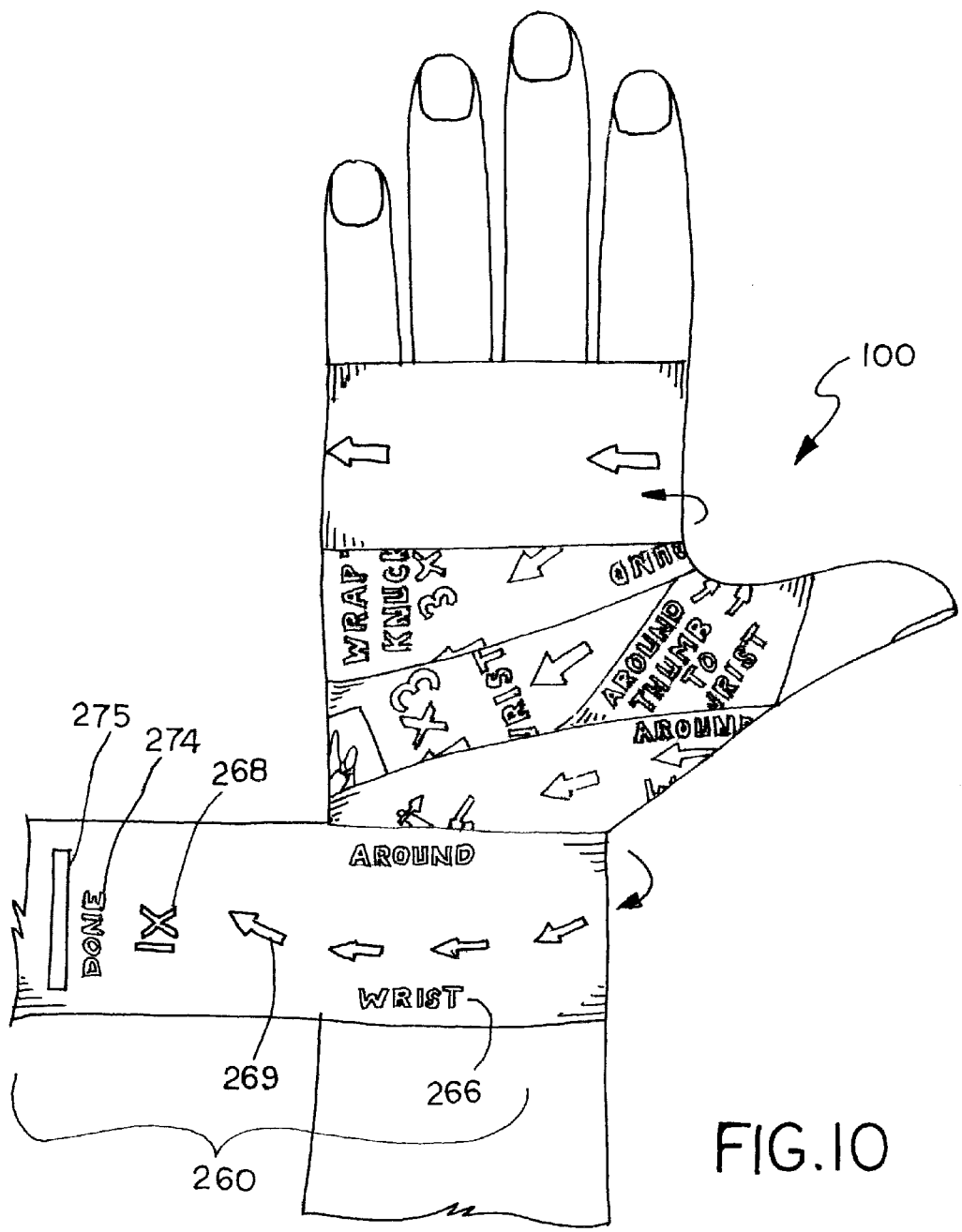
FIGS. 10 and 11 are top views of the hand wrap of FIG. 1 applied to a human hand, showing the sixth and final instruction step.
Figure 11:
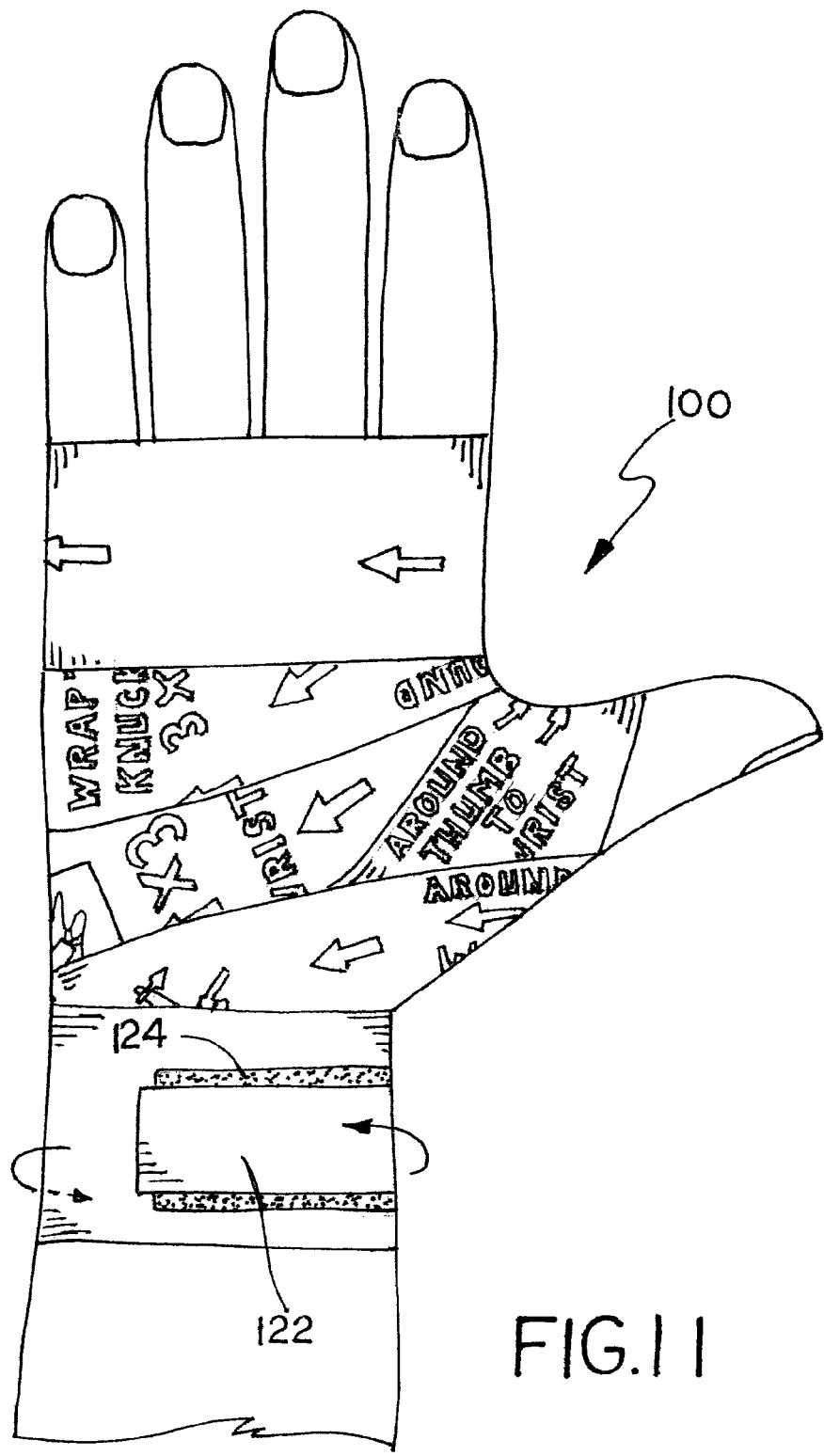
Figures 15, 16:
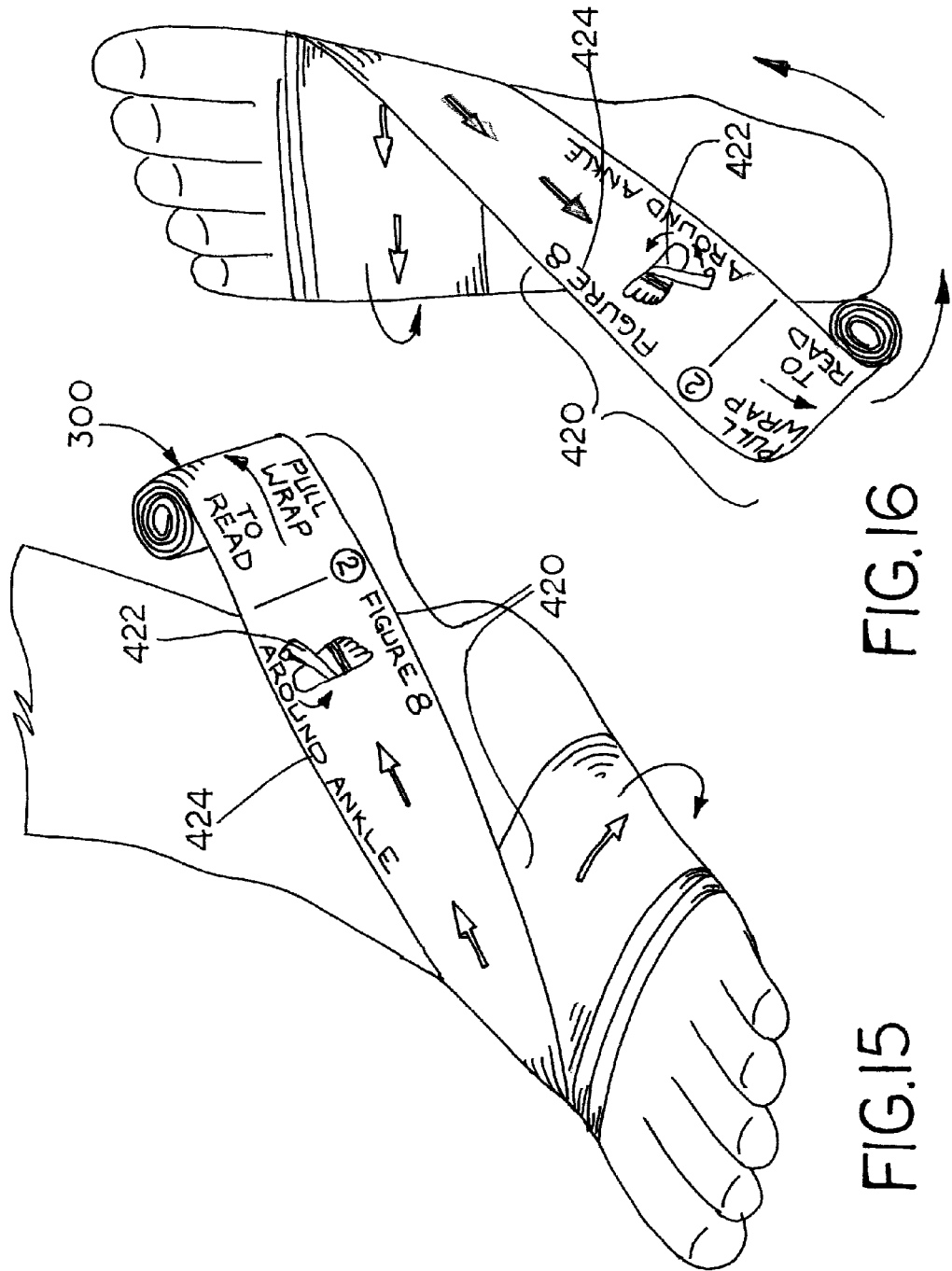
FIG. 15 is a perspective view of the wrap of FIG. 12 being applied to a human foot, showing the second instruction step.
FIG. 16 is a top view of the wrap of FIG. 12 being applied to a human foot, showing the second instruction step.
Figure 17:
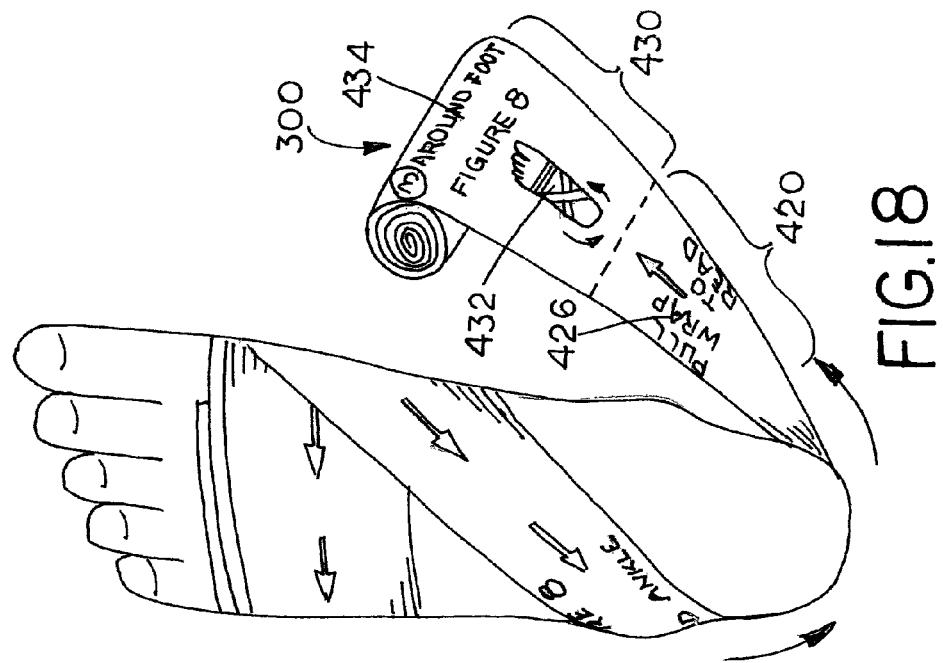
FIG. 17 is another perspective view of the wrap of FIG. 12 being applied to a human foot, further showing the second instruction step.
Figure 18:
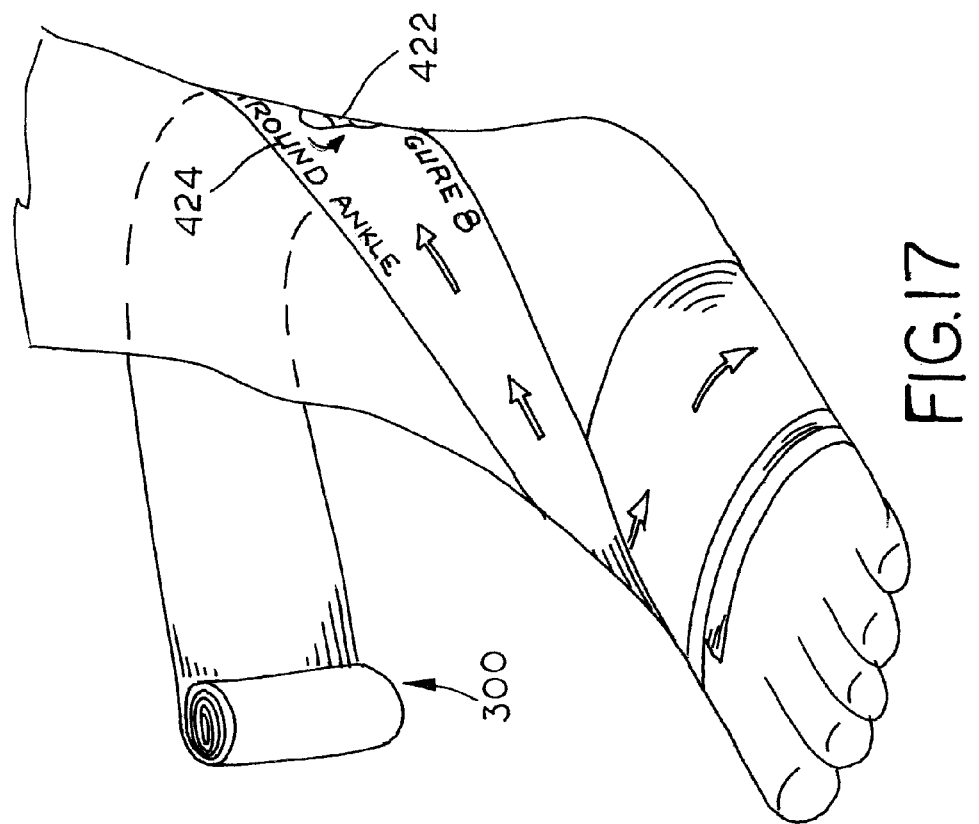
FIG. 18 is another top view of the wrap of FIG. 12 being applied to a human foot, further showing the second instruction step.

FIGS. 10 and 11 show the sixth and final step in applying the wrap to the user's hand. Once the fifth step is complete, instruction block 260 is visible. Instruction block 260 includes the word, "done" 264, a stop line 265, instruction text "around wrist" 266, instruction text "1×" 268 and arrows 269. Instruction block 260 also includes a final occurrence of the word "done" 274 and a final stop line 275. The instruction text "around wrist" 256 and "1×" 258 indicates that wrap 100 is wound around the wrist one time. Once the wrap is wound around the wrist, hook tab 120 is pressed against loop section 122 to secure tail end 104 to the rest of wrap 100.

FIGS. 12-25 show a second embodiment of the wraps of this invention, designated generally as reference numeral 300. As shown, wrap 300 is an elastic ankle wrap of the type used to bind and care for broken feet and ankles. Wrap 300 consists of a strip of woven elastic cloth with serialized graphic instruction sets 400 printed on both sides. Again, for purposes of simplicity and brevity, FIGS. 11-23 only illustrate the serialized graphic instruction sets 400 printed on one side of wrap 300. Instruction set 400 shown explains and depicts the application of wrap 300 counter-clockwise to a user's left foot. It should be understood that another instruction set (not shown) is printed on the opposite side of wrap 300, which explains and depicts the application of the wrap clockwise to a user's right foot and is printed on opposite side of wrap 300.

Instruction set 400 is similar to that of wrap 100 and is segmented into sequential instruction blocks (410, 420, 430, 440, 450, 460) spaced across the length of wrap 300, which direct the user for each step of applying wrap 300. Each instruction block 410, 420, 430, 440, 450 and 460 includes some combination of pictures, symbols, letters, numbers, abbreviations, and word texts that guide the user in the application of wrap 300 to the foot, whether to the user's own foot or a third person's foot. Again, each instruction step is readily visible to the user and is easily discernable as wrap 300 is applied. Instruction block 410, 420, 430, 440, 450 and 460 are selectively spaced along the between the lead end 302 and tail end 304, so that each instruction block is readily visible to the user and is easily discernable as wrap 300 and is unrolled and wound around the foot. Because of the elasticity of wrap 300, each instruction block includes the instruction text to "pull wrap to read", which prompts the user to pull the wrap tight so that the next instructions steps are readily visible over the top of the foot. Pulling the wrap tight not only ensure that the wrap is bound tightly around the ankle for support, but also positions the next instruction step on the wrap where it is readily visible.

FIGS. 12-23 illustrate how the wrap is applied to a user's left foot and how the serialize graphics instruction sets 400 provide a visible guide for the application of the wrap. FIGS. 13 and 14 shows the initial start for applying wrap 300 to the user's left foot. First, the lead end 302 of wrap 300 is placed overlying the top of the foot so that the first set of instruction block 410 is visible. Instruction block 410 includes a foot graphic 412, the word "start" 414, instruction text "around foot—wrap 3×" 416 and arrows 419.

FIGS. 15-18 show the second step in applying the wrap to the user's foot. Once the initial step is complete, instruction block 420 is visible. Instruction block 420 includes a foot graphic 422, instruction text "figure 8 around ankle" 424, instruction text "pull to read" 426 and arrows 429.

FIGS. 19 and 20 show the third step in applying the wrap to the user's foot. Once the second step is complete, instruction block 430 is visible. Instruction block 230 includes a foot graphic 432, instruction text "figure 8 around foot" 434, instruction text "pull to read" 436 and arrows 439.

FIGS. 21 and 22 show a fourth step in applying the wrap to the user's foot. Once the third step is complete, instruction block 440 is visible. Instruction block 440 includes a foot graphic 442, instruction text "figure 8 around ankle" 444, instruction text "pull to read" 446 and arrows 449.

FIGS. 23 and 24 show the fifth step in applying the wrap to the user's foot. Once the fourth step is complete, instruction block 450 is visible. Instruction block 250 includes a foot graphic 452, instruction text "figure 8 around foot" 454, instruction text "pull to read" 456 and arrows 459.

FIGS. 25 and 26 show the six and final step in applying the wrap to the user's foot. Once the fifth step is complete, instruction block 460 is visible. Instruction block 460 includes an arrow graphic 462, instruction text "around ankle 2×" 464, instruction text "pull to read" 466, the word "done" 467 and arrows 469. Once wrap 300 is wound around the ankle, tail end 304 is secured to the wrap with clips, safety pins or other fasteners (not shown).

It should be apparent from the foregoing that an invention having significant advantages has been provided. While the invention is shown in only a few of its forms, it is not just limited but is susceptible to various changes and modifications without departing from the spirit thereof. The embodiment of the present invention herein described and illustrated is not intended to be exhaustive or to limit the invention to the precise form disclosed. It is presented to explain the invention so that others skilled in the art might utilize its teachings. The embodiment of the present invention may be modified within the scope of the following claims.

I claim:

1. A flexible wrap for an appendage comprising:
    an elongate strip of flexible material adapted to be rolled onto itself and unrolled from itself while being wrapped repeatedly around the appendage, the strip having a first end and an opposite second end, the strip also having an inner side and an opposite outer side;
    an instruction set printed on the outer side across the length of the strip between the first end and the second end set for explaining and illustrating the application of the wrap to an appendage, the instruction set includes a plurality of instruction blocks where each of the plurality of instruction blocks is spaced apart from one another and selectively located along the length of the strip to be visible after the completion of the subsequent step for applying the wrap repeatedly around the appendage and provides sequential visible directions and illustrations of the next step for applying the wrap to the appendage as the wrap is unrolled.

2. The wrap of claim 1 wherein each of the plurality of instruction blocks includes written text directions and graphics.

3. The wrap of claim 1 wherein the plurality of instruction blocks includes a first instruction block printed to the outer side adjacent the first end and a last instruction block printed on the outer side adjacent the second end.

* * * * *